United States Patent [19]

Rosenfeldt

[11] 4,351,634
[45] Sep. 28, 1982

[54] PRIORITY SYSTEM DENTAL INSTRUMENT DELIVERY

[75] Inventor: Wolfgang Rosenfeldt, Bad Bergzabern, Fed. Rep. of Germany

[73] Assignee: Sybron Corporation, Rochester, N.Y.

[21] Appl. No.: 150,056

[22] Filed: May 15, 1980

[51] Int. Cl.³ .............................................. A61C 1/02
[52] U.S. Cl. ...................................... 433/28; 433/98; 307/38
[58] Field of Search .................... 433/28, 27, 98, 101; 307/38, 39

[56] References Cited

U.S. PATENT DOCUMENTS

| 2,712,101 | 6/1955 | Salati | 307/38 |
| 3,629,599 | 12/1971 | Zuckerman | 307/38 |
| 4,066,913 | 1/1978 | Manning et al. | 307/38 |
| 4,114,273 | 9/1978 | McGaha | 433/27 |

FOREIGN PATENT DOCUMENTS

| 2636957 | 2/1978 | Fed. Rep. of Germany | 433/98 |
| 2730676 | 1/1979 | Fed. Rep. of Germany | 433/98 |
| 2733916 | 2/1979 | Fed. Rep. of Germany | 433/28 |

*Primary Examiner*—Gene Mancene
*Assistant Examiner*—John J. Wilson
*Attorney, Agent, or Firm*—Theodore B. Roessel; J. Stephen Yeo

[57] ABSTRACT

A dental delivery unit carries a number of dental instruments in nests. Upon selection, one nest is extended carrying its instrument to the dentist's group. Selection is accomplished by a priority system. Associated with each nest is a switch. Activation of any switch starts a selection period by a priority system. At the end of the selection period the nest corresponding to the last to be activated switch is extended by the priority system.

If two switches are activated together the nest corresponding to the furthermost switch is extended.

1 Claim, 5 Drawing Figures

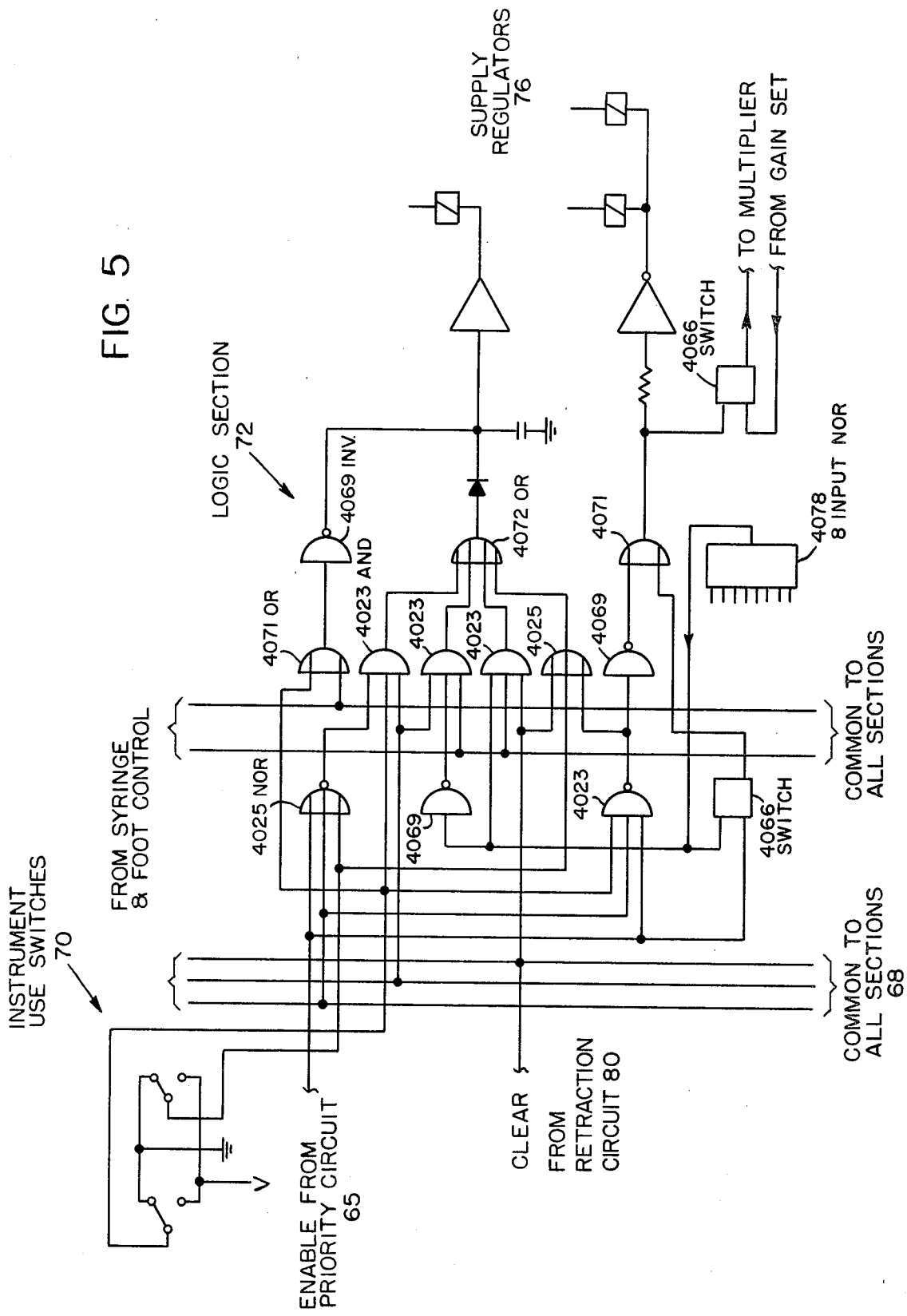

PRIORITY SYSTEM DENTAL INSTRUMENT DELIVERY

BACKGROUND OF THE INVENTION

This invention relates to dental instruments and more particularly, is concerned with delivery units for dental delivery instruments. In a copending patent application (Ser. No. 150,050, filed May 15, 1980) there is disclosed a dental unit which holds a plurality of instruments in individual nests. The nests are moved to a storage position to an in-use position. Upon selection by the dentist the nest and the instrument it holds is moved from its storage position through an arcuate path of travel to place the instrument tangently onto the palm of the dentist.

Each nest is selected by switching a corresponding switch. Only one instrument is used at a time. The selection switches are grouped together and it is conceivable two or more switches may accidentally be switched either simultaneously or sequantally.

Accordingly, it is an object of this invention to provide means to assure that only one nest is extended to an in-use position. Another object of the invention is to provide means to increase the likelihood that the correct nest is extended in the presence of contradictory switching.

SUMMARY OF THE INVENTION

A dental delivery unit carries a number of dental instruments in nests. Upon selection, one nest is extended carrying its instrument to the dentist's group. Selection is accomplished by a priority system. Associated with each nest is a switch. Activation of any switch starts a selection period by a priority system. At the end of the selection period, the nest corresponding to the last to be actuated switch is extended by the priority system.

If two switches are actuated together, the nest corresponding to the further switch is extended.

BRIEF DESCRIPTION OF THE DRAWINGS

FIG. 5 is a schematic drawing of microswitches and logic associated with each instrument of unit.

DESCRIPTION OF THE INVENTION

Figure 1:
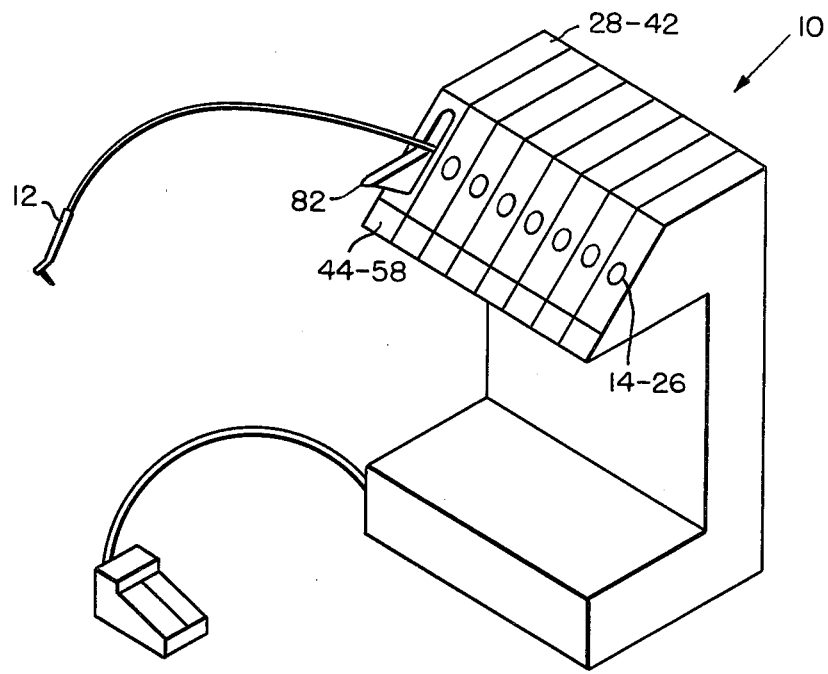
FIG. 1 shows a dental instrument delivery unit including the delivery priority system of the present invention.

FIG. 1 represents a dental instrument delivery unit 10 which holds a plurality of dental instruments 12–26 in individual nests 28–42. Connected to each nest are extending means for moving each nest from a stored position to an extending in-use position within the grasp of the dentist. The nest and extending means are the subjects of a copending patent application (U.S. Ser. No. 240,486 filed Mar. 4, 1981). Corresponding with each nest is an instrument selection switch 44–58 which when activated gives a signal used by the priority circuit in chosing the priority of an instrument. The switches 44–58 are preferably proximity switches of the sealed capacitor type.

Figure 2:
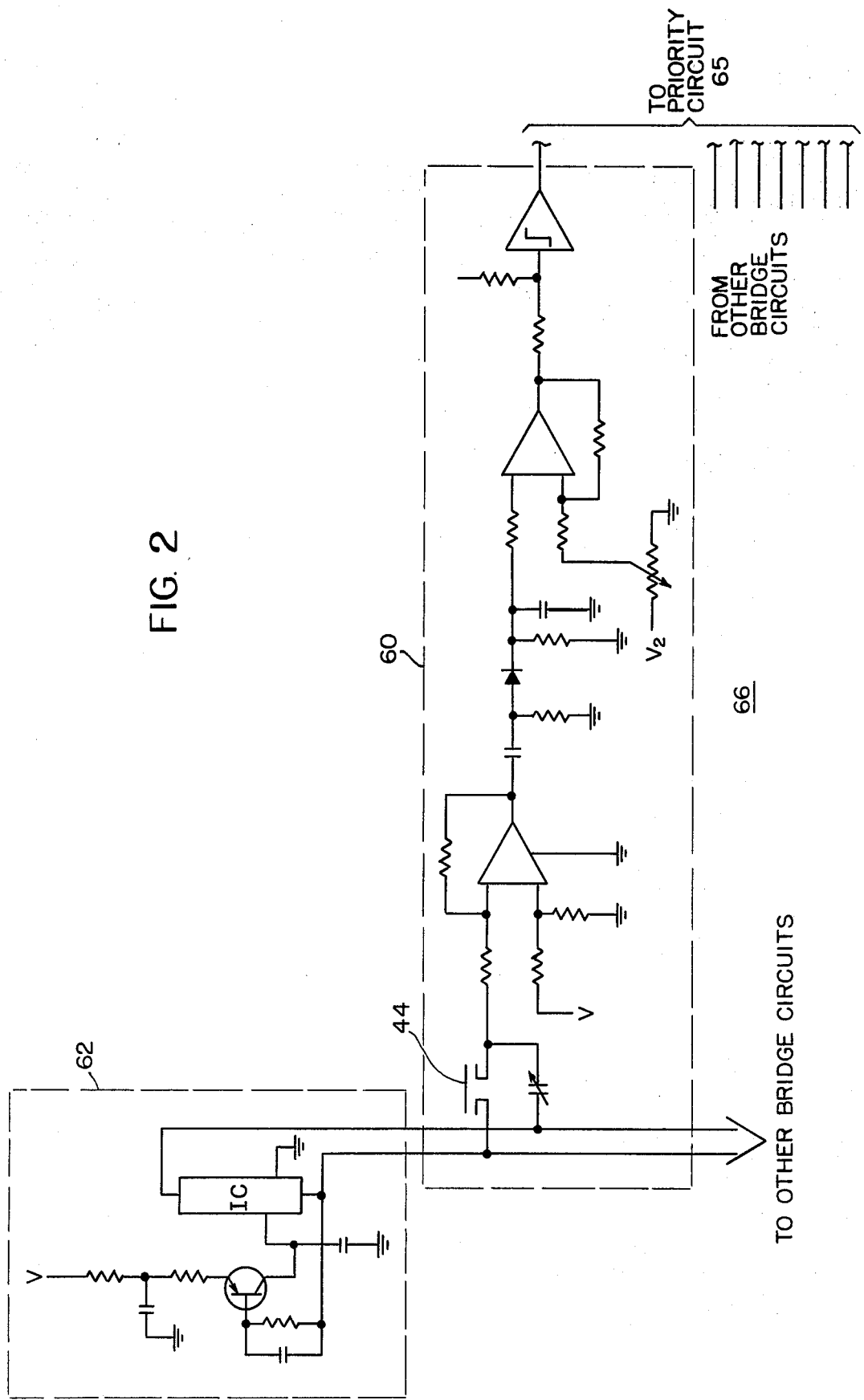
FIG. 2 illustrates an instrument selection switch circuit used in the unit.

As seen in FIG. 2, each capacitor switch 44 is part of a capacitive bridge circuit 60. All the bridge circuits are supplied by a single high-frequency oscillator 62. A finger touching or in proximity to a switch imbalances its bridge circuit to produce a signal. The signal is amplified by a amplifier and directed to a priority circuit discussed later.

Returning to FIG. 1, unit 10 is intended to be located near the right hand side of the dentist. The selection switches 44–55 are closely arranged and it is possible that two or more switches could be accidentally activated simultaneously or sequentially. In practice on one instrument is to be used at a time, therefore, a delivery priority system has been developed for determining which instrument is to be released if two or more selection switches are actuated.

Figure 3:
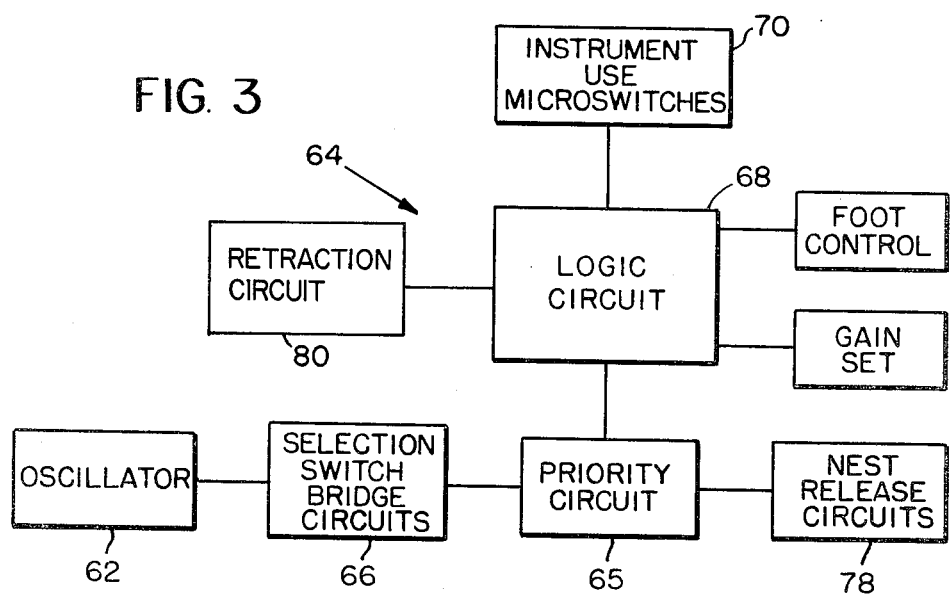
FIG. 3 is a block diagram of the dental unit including the priority system.

FIG. 3 is a block diagram which includes a delivery priority system 64 according to the invention. A delivery priority circuit, seen in schematic form in FIG. 4, determines instrument priority on the basis of signals received from instrument selection switch circuit 66 which includes all the bridge circuits, and logic circuit 68.

The priority circuit 65 provides for a selection period which starts to run upon the first activation of a switch. The priority circuit delays final choice until the expiration of the selection period. The delay allows corrections in the case of an inadvertent selection. Thus, if two instrument selection switches are touched sequentially in time, within the selection period, the priority circuit will choose the instrument corresponding to the switch touched last within the selection period.

There are eight selection switches 44–58 which are part of eight corresponding bridge circuits 66 of which 60 is representative.

Priority circuit 65 will now be described with reference to FIG. 4. The outputs of the eight bridge circuits 66 are directed to a 8-bit priority encoder 84 that encodes the highest priority input into a three bit binary code. The eight inputs D7 through D0 each have an assigned priority with D7 having the highest priority and D0 having the lowest. The bridge circuit associated with the selection switch further from the dentist is connected to D7, whereas the bridge circuit corresponding to the nearest selection switch is connected to D0. When encoder 84 is enabled, a three bit binary representation of the highest priority input appears on the output lines and is connected from the encoder to a D-latch circuit 86 which holds the state of the three bit binary output when clocked. A change in level on any of the three bit outputs of the D-latch circuit 86 (because of activation of a selection switch) triggers a pair of monostable multivibrators 88, 90 and starts the running of the selection period. Monostable multivibrators 88, 90 return to their stable state after a predetermined length of time ending the selection period. An output is provided to one input of each of eight two-input AND gates 92–106 and the D-latch circuit 86 is clocked. The three bit output from the D-latch 86 is directed through inverters 108–112 to a three bit to octal decoder 114 having eight outputs connected to the remaining inputs of the AND gates 92–106 and to the circuit 68 enabling the corresponding block of logic. Only one AND gate input will have the signal, which is dependent upon the three bit binary input. This AND gate will give an output signal which will trigger the nest-release circuit 78 which corresponds to the selection switch having priority. The nest-release circuit 78 includes a switching transistor 116 which energizes a relay 118 for actuating the release of an instrument nest.

If two switches are actuated together as the last selection within the selection period, the instrument priority is chosen in such a way that in the case of equally strong instrument selection switch signals arriving simultaneously priority is given to the signal from leftmost selection switch as seen by the viewer. In other words if two selection switches are actuated simultaneously, only the instrument corresponding to the switch furthermost from a right handed dentist would be chosen. This is because the selector switches nearest the dentist are more likely to be "brushed" against accidentally.

At the expiration of the selection period the logic circuit detects and stores the priority of the chosen instrument. The corresponding nest is extended by actuators 82 (seen in FIG. 1) corresponding to the nest upon the receipt of a release signal from release circuits 78 connected to the priority circuit. Microswitches arranged with the nests inform the logic when the nest is fully in a stored position or fully extended.

FIG. 5 shows the microswitches 70 and the portion of the logic 72 associated with each instrument. The portion of the logic 72 shown is interconnected to identical logic of the other instruments to form the logic circuit 68 of FIG. 3.

The chosen instrument is functionally enabled by the logic circuit 68 by connecting a control signal from control 74 to the appropriate supply regulators 76. The other instruments are non-functional and may be withdrawn from the unit 10 for service by the dental assistant and returned without affecting the function of the chosen instrument.

When the chosen instrument is to be returned to its nest, the dentist triggers a retraction circuit 80. The retraction circuit sends a signal which clears the logic 68 and resets the system 64.

Figure 4:
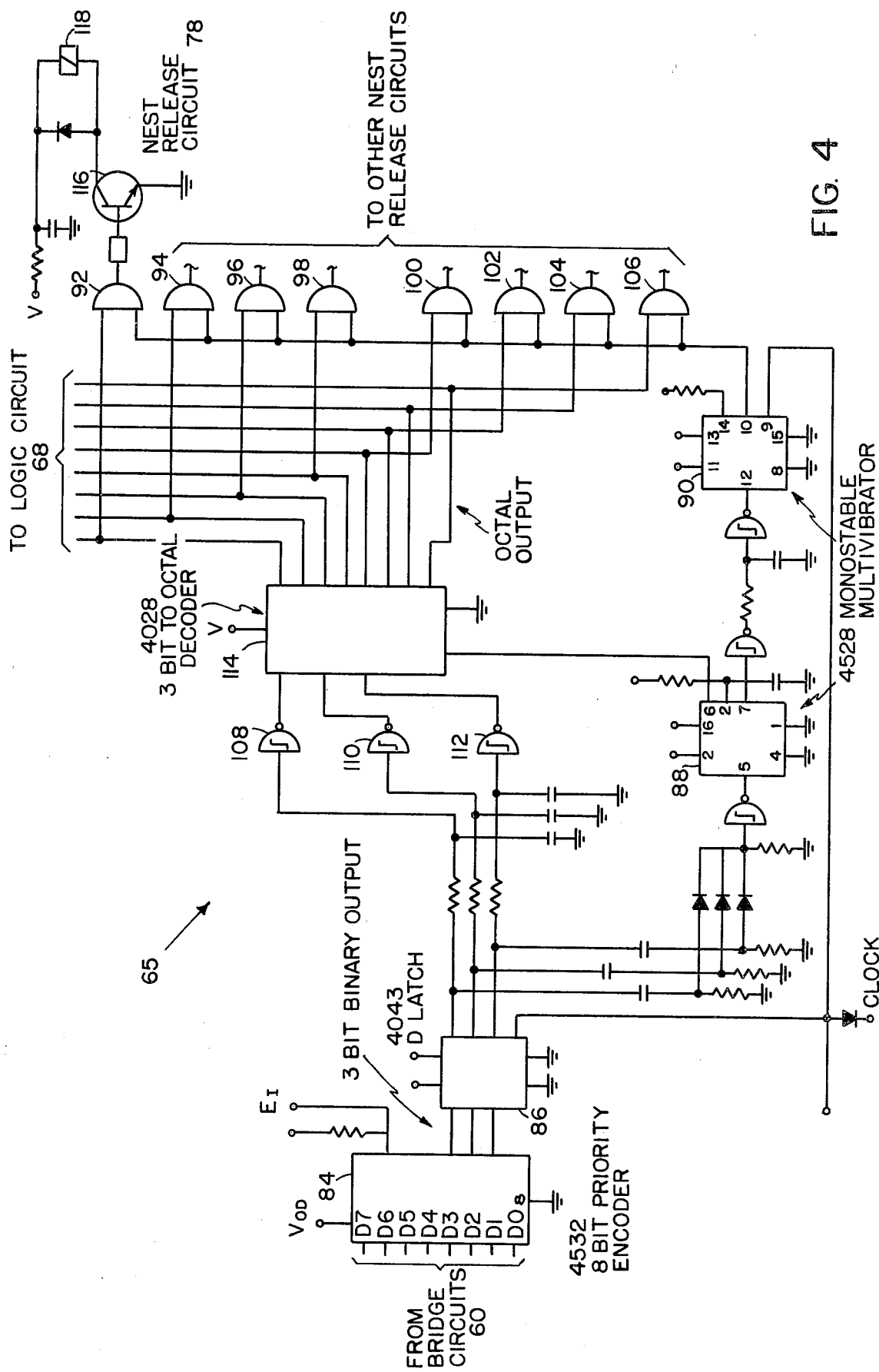
FIG. 4 is a schematic representation of a priority circuit used in the priority system.

|  | IC Functions | |
|---|---|---|
|  | Number | Function |
| FIG. 4 (priority circuit | 4028 | 3 Bit Binary to Octal |
|  | 4042 | Quad Clocked "D" Latch |
|  | 4528 | Dual Monostable Multivebrator |
|  | 4532 | 8-Bit Priority Encoder |
| FIG. 5 (logic) | 4023 | Triple 3-Input NAND Gate |
|  | 4025 | Triple 3-Input NOR Gate |
|  | 4066 | Quad Bilateral Switch |
|  | 4069 | Hex Inventor |
|  | 4071 | Quad 2-Input OR Gate |
|  | 4072 | Dual 4-Input OR Gate |
|  | 4073 | Triple 3-Input ANO Gate |
|  | 4078 | 8-Input NOR Gate |

Having described the invention, I claim:

1. A dental instrument delivery unit having a delivery priority system comprising:
   a dental unit holding a plurality of dental instruments in individual nests;
   an instrument selection switch corresponding to each nest and providing a signal upon activation by an operator;
   extending means corresponding to each instrument selection switch for extending the nest corresponding to that switch upon receipt of a release signal;
   a priority circuit which provides a selection period running from the first time any instrument selection switch is activated, and upon expiration of the selection period causes a release signal to be directed to the extending means corresponding to the instrument selection switch last activated within the selection period, or if two instrument selection switches are simultaneously activated last, directing a release signal to the extending means corresponding to the activated switch futhermost from the operator.

* * * * *